United States Patent [19]

Morelle et al.

[11] 4,208,421
[45] Jun. 17, 1980

[54] THERAPEUTIC COMPOSITIONS FOR THE TREATMENT OF CONNECTIVE TISSUES DISEASES

[76] Inventors: Jean Morelle; Eliane Lauzanne-Morelle, both of 170 avenue Parmentier, 75010 Paris, France

[21] Appl. No.: 890,906

[22] Filed: Mar. 27, 1978

Related U.S. Application Data

[63] Continuation of Ser. No. 493,503, Aug. 1, 1974, abandoned, which is a continuation of Ser. No. 283,828, Aug. 25, 1972, abandoned.

[51] Int. Cl.$^2$ .................. A61K 31/40; C07D 207/12
[52] U.S. Cl. ........................... 424/274; 260/326.46
[58] Field of Search .................. 424/274; 260/326.46

[56] References Cited

U.S. PATENT DOCUMENTS

| | | | |
|---|---|---|---|
| 3,016,334 | 1/1962 | Lewis | 424/95 |
| 3,891,765 | 6/1975 | Coirre et al. | 424/274 |
| 3,932,638 | 1/1976 | Coirre et al. | 424/274 |
| 3,997,559 | 12/1976 | Coirre et al. | 424/274 |

FOREIGN PATENT DOCUMENTS 1485602 of 1967 France .
1491262 of 1967 France .
1153408 5/1969 United Kingdom .

OTHER PUBLICATIONS

French, Brevets Speciaux de Medicaments #51, 12/1968, p. 1358, Abst. of French Medical Patent 6.475M, 5/1967.
Biochemistry, vol. 2, 1963, pp. 58–66 (Piez et al.)
Tadashi et al., Chem. Abst. 66, 29058(y) (1967).

*Primary Examiner*—Douglas W. Robinson
*Attorney, Agent, or Firm*—Eyre, Mann, Lucas & Just

[57] ABSTRACT

A therapeutic composition for the external treatment of the diseases of connective tissues wherein the active ingredient is a compound of the formulae:

Formula 1—O-lipoylhydroxyproline

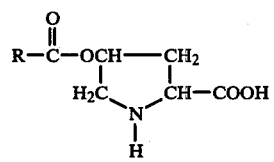

Formula 2—N-lipoylhydroxyproline

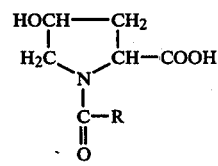

Formula 3—O,N-dilipoylhydroxyproline

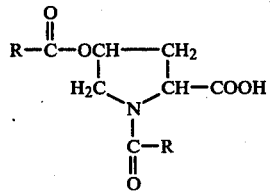

dosed at 5 to 10% in weight of the complete composition.

7 Claims, No Drawings

THERAPEUTIC COMPOSITIONS FOR THE TREATMENT OF CONNECTIVE TISSUES DISEASES

This is a continuation of application Ser. No. 493,503 filed Aug. 1, 1974 which in turn was a continuation of application Ser. No. 283,828 filed Aug. 25, 1972 both now abandoned.

The present invention relates to new therapeutic compositions, the active ingredients of which are lipoyl derivatives of hydroxyproline.

The structure of these active ingredients may be represented by the following formulae, wherein R, in each case, stands for an hydrocarbon chain containing from 6 to 30 carbon atoms.

Formula 1—O-lipoylhydroxyproline

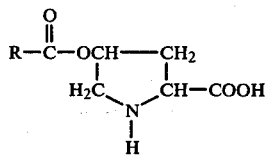

Formula 2—N-lipoylhydroxyproline

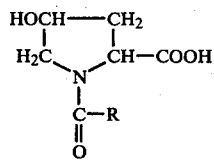

Formula 3—O,N-dilipoylhydroxyproline

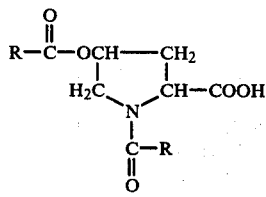

The interest of these compositions lies at first
in the fact that hydroxyproline is an important constituen of collagen wherein its content is from 9 to 15%; frequently the diseases of connective tissues are in relationship with hydroxyproline which has been proved to play an important part for keeping the collagen in a heathly condition; moreover it has been found by the biosynthesis of hydroxyproline from $C^{14}$ labelled proline that hydroxyproline is an agent in the synthesis of collagen; secondly,
in the fact that the lipoyl part of these derivatives gives a good liposolubility and allows a good penetration of the product through the skin, towards the connective tissues; and finally
it has been found that structures combining a fatty acid and an aminoacid are specially favourable for the in situ synthesis of proteins in the body.

Various recent experiments have shown that structures of this kind are specially interesting as carriers of the aminoacids through the skin.

As collagen is the most important part of the human proteins (about 40%) it is important to prevent or delay any structural alteration in relationship with the senescence or with pathological perturbations that could result in many cases either in arthrosis with the associated painful inconveniences or in various sclerosis.

This is the reason why it has been developed, according to the invention, a new easily assimilable form of one of the most important aminoacid, i.e. hydroxyproline for the treatment of the connective tissues.

The synthesis of the above mentioned structure is undertaken by the usual methods: for instance, according to the SCHOTTEN-BAUMANN reaction, by reacting a fatty acid chloride on hydroxyproline or by the direct reaction of the fatty acid on hydroxyproline in the presence of compounds such as dicyclocarbodiimide or N-hydroxysuccinimide.

Although the dilipoylhydroxyproline derivatives are generally more interesting than the corresponding monolipoyl ones (the lipo solubility of the dilipoyl is higher than the same of mono), all these lipoyl derivatives are similarly encompassed by the invention.

I.—GENERAL FEATURES

To give an idea about the active ingredients of the therapeutic compositions of the invention, some physical characteristics are reported below:

(a) Form

These compounds are generally white powders when the lipoyl part corresponds to a saturated acid; alternatively, in the case of an insaturated acid, the compounds are either pasty or liquid.

(b) Solubility

The solubility of these active agents is a peculiar one due to their special structures. Solubility is poor in either polar or non polar solvents but good or very good in mixture of polar + non polar solvents.

For instance, solubility has been tested in ethanol, chloroforme, methylene chloride, benzene, petrolic ether and water. These agents reveal no solubility in water, benzene and methylene chloride and a very poor solubility in petrolic ether, ethanol, chloroforme and mixture of ethanol and water.

Adversely these compounds show a very good solubility in mixtures such as chloroforme + ethanol or ethanol + methylene chloride or benzene + ethanol or petrolic ether + ethanol.

These remarks apply to mono or dilipoyl derivatives wherein the acyl rest is palmitoyl, oleoyl, lauryl, stearoyl or linoleyl.

(c) Acidity and acid numbers

In this field the active agents of the invention show also a very specific action. It is, at first, to be noticed that hydroxyproline which is the common moiety to all the compounds of the invention has a high acid number (427); however the aqueous solution at 1% gives only a pH value of 6, although the water solubility of hydroxyproline be very good.

The special features of these compounds would be better understood on the example of O,N-dipalmitoyl hydroxyproline.

Taking in account the number of carboxy group, the same number carboxy groups as in a 1% solution of hydroxyproline will be obtained by 4.6 times the amount of hydroxyproline. A 1% solution of hydroxyproline giving a pH value of 6, the 4.6% dispersion of O,N-dipalmitoylhydroxyproline gives a pH value of 5 in cool water.

Moreover, after heating the dispersion, the pH reach the figure of 4. It is thus noticed that the lower pH is obtained by a dispersion of the water-insoluble product, the acid number of which is the lowest (92 compared to the 427 of hydroxyproline). The above mentioned experiments on a hydroxyproline solution and an O,N-dipalmitoylhydroxyproline dispersion in water may be repeated when using on both mixtures an emulsifying agent like polyoxyethylene derivatives.

In these new conditions, there is obtained a pH value of 5.4 for hydroxyproline whereas, for the dispersion of O,N-dipalmitoylhydroxyproline, the pH value is from 3.4 to 3.5.

These experiments show the special character of the biologic acidity which is specific of this class of compounds.

Some analytical values are hereunder reported for preparations of above agents confirming the invention wherein about 10% of free fatty acid are present.

| Active agents | Nitrogen % theoric | Nitrogen % found | Acid index theoric | Acid index found | Melting point |
|---|---|---|---|---|---|
| N-palmitoyl hydroxyproline | 3.79 | 3.86 | 151 | 162 | #80° |
| O,N-dipalmitoyl hydroxyproline | 2.13 | 1.96 | 92 | 102 | #60° |
| O,N-dioleoyl hydroxyproline | 2.12 | 1.94 | 84 | 92 | — |

II.—TOXICITY

This kind of compounds does not show any toxicity. The mono and dilipoyl derivatives of hydroxyproline wherein the lipoyl part is palmitoyl, oleoyl, lauryl, stearoyl, linole, have been administered per os, each, to 10 mice, as a suspension in peanut oil. At the maximum dose of 3 g per kg, for 10 days, neither death nor any symptom of disease could be noticed. Moreover the weight evolution of the administered mice is perfectly similar to this one of the controlled animals administered only with pure peanut oil.

III.—INDICATIONS

These compounds are to be used in preparations for the treatment of any form of biochemical unbalance of the connective tissues such as for instance rheumatismal disease arthrosis pains, chronic articulary affections of inflammatory or non inflammatory origin, tissular deformations, cardio vascular diseases and as general cutaneous anti-inflammatories.

IV.—PRESENTATIONS

Experimentations have proved that cream and milk compositions for local applications must contain 5 to 10% in weight of active agent. Higher contents of active material do not result in a better action and are therefore unnecessary.

Four examples of compositions according to the invention are given below.

In each occurence, parts are given in weight.

| Formula A (cream) | |
|---|---|
| Stearic acid | 7 |
| Cetylic alcohol | 5 |
| Perhydrosqualene | 5 |
| Isopropyle palmitate | 5 |
| Glycerol | 10 |
| O,N-dipalmitoyl hydroxyproline | 5 |
| Water sufficient amount to | 100 |
| Formula B (cream) | |
| Polyethyle cetylic alcohol | 15 |
| Perhydrosqualene | 10 |
| Glycerol | 10 |
| O,N-dioleoyl hydroxyproline | 7 |
| Water sufficient amount to | 100 |
| Formula C (cream) | |
| Triethanolamine stearate | 12 |
| Glycerol | 10 |
| Perhydrosqualene | 10 |
| N-stearoyl hydroxyproline | 7 |
| Water, sufficient amount to | 100 |
| Formula D (milk) | |
| Glycerol stearate | 7 |
| Perhydrosqualene | 3.5 |
| Isopropyl palmitate | 3.5 |
| N-linoleyl hydroxyproline | 10 |
| Water, sufficient amount to | 100 |

V.—POSOLOGY

To be applied locally on the skin close to the portion of body to be cured, 2 to 3 times a day until a satisfactory result is obtained (from some days to some weeks).

We claim:

1. A composition of matter consisting essentially of O-lipoylhydroxyproline of the formula

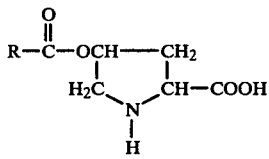

wherein R is a lypoyl hydrocarbon radical having from 6 to 30 carbon atoms.

2. A composition of matter consisting essentially of N-lipoylhydroxyproline of the formula

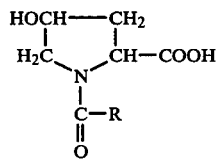

wherein R is a lipoyl hydrocarbon radical having from 6 to 30 carbon atoms.

3. A composition of matter consisting essentially of O,N-dilipoylhydroxyproline of the formula

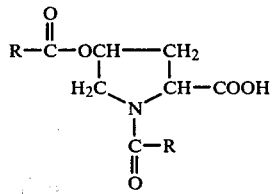

wherein R is a lipoyl hydrocarbon radical having from 6 to 30 carbon atoms.

4. A method for the treatment of algias and inflammations caused by biochemical unbalance of the connective tissues of humans comprising applying topically to the skin from two to three times per day a therapeutic composition consisting essentially of a pharmaceutically acceptable carrier and incorporated in said carrier an amount within the range from 5% to 10% by weight of the finished composition of a compound selected from the group consisting of:

(a) O-lipoylhydroxyproline

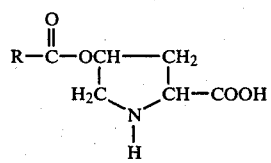

(b) N-lipoylhydroxyproline

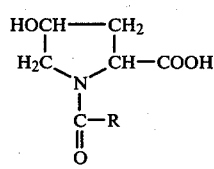

and
(c) O,N-dilipoylhydroxyproline

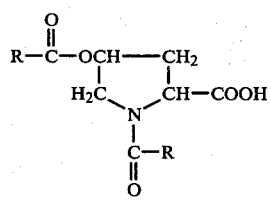

wherein R is a lipoyl hydrocarbon radical having from 6 to 30 carbon atoms and wherein the carrier for said compound is a carrier in which said compound is soluble, said carrier comprising at least one polar liquid and at least one non-polar liquid, said polar and non-polar liquids being compatible.

5. The method of claim 4 wherein said compound is N-palmitoylhydroxyprolinic acid.

6. A method for the treatment of algias and inflammations caused by biochemical unbalance of the connective tissues of humans comprising applying topically to the skin from two to three times per day a therapeutic composition consisting essentially of a pharmaceutically acceptable carrier and incorporated in said carrier an effective amount within the range from 5% to 10% by weight of the finished composition of a compound selected from the group consisting of:

(a) O-lipoylhydroxyproline

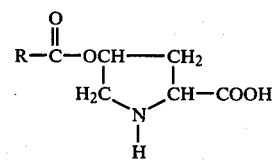

(b) N-lipoylhydroxyproline

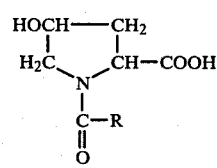

and
(c) O,N-dilipoylhydroxyproline

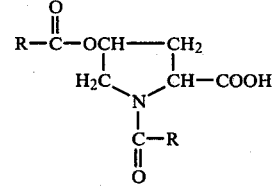

wherein R is a lipoyl hydrocarbon radical having from 6 to 30 carbon atoms.

7. The method of claim 6 wherein said compound is N-palmitoylhydroxyprolinic acid.

* * * * *

UNITED STATES PATENT AND TRADEMARK OFFICE
CERTIFICATE OF CORRECTION

PATENT NO. :  4,208,421

DATED      :  June 17, 1980

INVENTOR(S):  Jean Morelle et al.

It is certified that error appears in the above-identified patent and that said Letters Patent is hereby corrected as shown below:

Front page of the patent, after the entry on "Related U.S. Application Data" and before the line beginning "[51] Int.Cl.²", insert the following:

[30]     Foreign Application Priority Data

Sept. 16, 1971   France............... 71 33331

Signed and Sealed this

Seventeenth Day of June 1986

[SEAL]

Attest:

DONALD J. QUIGG

Attesting Officer

Commissioner of Patents and Trademarks